United States Patent [19]
Fischer et al.

[11] Patent Number: 5,623,040
[45] Date of Patent: Apr. 22, 1997

[54] POLYMERISABLE PHOTOCHROMIC NAPHTHACENEDIONES, POLYMERS OF THESE MONOMERS, PROCESS FOR THEIR PREPARATION AND THE USE THEREOF

[75] Inventors: Evelyn Fischer, Weil am Rhein, Germany; Walter Fischer, Reinach, Switzerland

[73] Assignee: Ciba-Geigy Corporation, Tarrytown, N.Y.

[21] Appl. No.: 510,453

[22] Filed: Aug. 2, 1995

Related U.S. Application Data

[62] Division of Ser. No. 135,775, Oct. 12, 1993, Pat. No. 5,488,119.

[30] Foreign Application Priority Data

Oct. 15, 1992 [CH] Switzerland ............................. 3216/92

[51] Int. Cl.⁶ .......................... C08F 12/32; C08F 112/32
[52] U.S. Cl. .......................... 526/284; 427/553; 430/541
[58] Field of Search .......................... 526/284; 427/553; 430/541

[56] References Cited

U.S. PATENT DOCUMENTS

| | | | |
|---|---|---|---|
| 3,985,566 | 10/1976 | Buhr et al. | 526/316 |
| 4,193,927 | 3/1980 | Baumann et al. | 260/326.26 |
| 5,177,227 | 1/1993 | Fischer et al. | 552/201 |
| 5,206,395 | 4/1993 | Fischer et al. | 552/201 |
| 5,208,354 | 5/1993 | Fischer et al. | 552/200 |
| 5,300,663 | 4/1994 | Fischer et al. | 552/202 |

FOREIGN PATENT DOCUMENTS

| | | |
|---|---|---|
| 0132221 | 1/1985 | European Pat. Off. |
| 0134752 | 3/1985 | European Pat. Off. |
| 0162017 | 11/1985 | European Pat. Off. |
| 0182745 | 5/1986 | European Pat. Off. |
| 0401791 | 12/1990 | European Pat. Off. |
| 0438376 | 7/1991 | European Pat. Off. |
| 0489689 | 6/1992 | European Pat. Off. |
| 1962588 | 5/1979 | Germany. |

OTHER PUBLICATIONS

Derwent Abstract No. 92–193849/24.
Derwent Abstract No. 91–217048/30.
Derwent Abstract No. 90–369843/50.
Derwent Abstract No. 86–139104/22.
Derwent Abstract No. 85–291223/47.
Derwent Abstract No. 85–070066/12.
Derwent Abstract No. 85–020528/04.
Derwent Abstract No. 70–49840R/28.

Green et al., J. Macromol. Sci.–Revs. Macro. Chem. C21(2), (1981–1982) pp. 187–273.

Delzenne, Adv. Photochem., vol. 11, (1979) pp. 1–103.

*Primary Examiner*—Thomas Hamilton, III
*Attorney, Agent, or Firm*—George R. Dohmann

[57] ABSTRACT

Compounds of formulae I and II

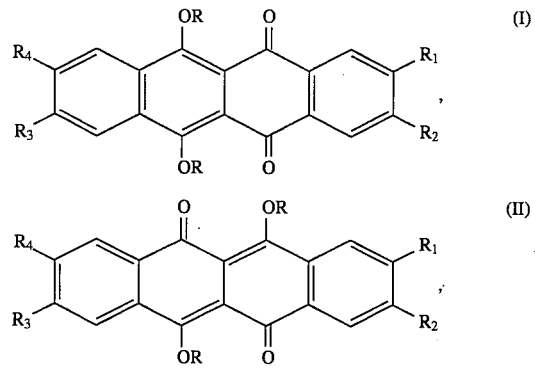

wherein R is phenyl and $R_1$ to $R_4$ are H or a substituent such as phenylthio, and one of the substituents $R_1$, $R_2$, $R_3$ and $R_4$ is a group of formula III $$-X-C(O)-CR_5=C(R_6)_2 \qquad (III)$$

or R is substituted by a group of formula III, wherein X is a linking group or $-X-C(O)-$ is a direct bond, and $R_5$ and $R_6$ are each independently of the other H, halogen, $C_1-C_{12}$alkyl or $C_6-C_{10}$aryl, can be polymerised to homopolymers or copolymers. The monomers and polymers are reversible photochromic systems which can be used as colour indicators, as photochemically modifiable colour filters, or for the optical storage of information.

10 Claims, No Drawings

POLYMERISABLE PHOTOCHROMIC NAPHTHACENEDIONES, POLYMERS OF THESE MONOMERS, PROCESS FOR THEIR PREPARATION AND THE USE THEREOF

This is Divisional of Ser. No. 08/135,775, filed Oct. 12, 1993, now U.S. Pat. No. 5,488,119.

The present invention relates to photochromic naphthacene-5,12-diones which carry 1 or 2 aryloxy groups in 6-position or in 6- and 11-positions, and which contain an ethylenically unsaturated group; to the anaquinones thereof; to homopolymers or copolymers of these monomers with radically polymerisable ethylenically unsaturated comonomers; to their preparation and to the use thereof for the optical storage of information, for contrast and colour formation, and as photochemically modifiable colour filters.

Photochromic naphthacene-5,12-diones which are substituted in 6- and/or 11-positions by an aryloxy group are disclosed in EP-A-0 438 376 and EP-A-0 489 689. The proposal is also made in these publications to incorporate these compounds in polymers for different utilities. Owing to their unsatisfactory solubility, it is not always possible to achieve the desired concentrations or a sufficiently uniform dispersion of these compounds in the polymers.

Surprisingly, it has now been found that such naphthacene-5,12-diones retain their photochromism if they contain radically polymerisable ethylenically unsaturated groups. The monomers can also be homopolymerised or copolymerised with ethylenically unsaturated compounds. It is then posssible to prepare from the polymers uniform photochromic layers with defined and also large amounts of photochromic groups, whereby uniform and superior colour intensities can be achieved. The monomers and polymers are thermally very resistant and have low susceptibility to oxidation.

In one of its aspects the invention relates to compounds of formulae I and II

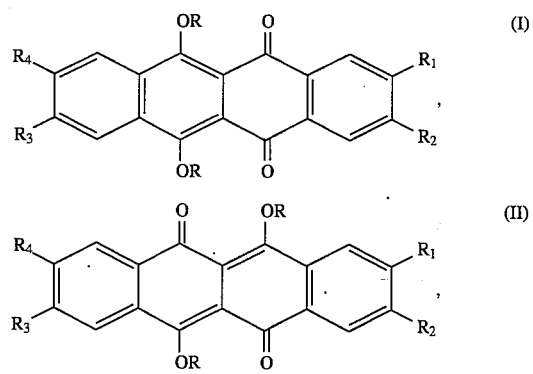

wherein R is unsubstituted $C_6$–$C_{14}$aryl or $C_6$–$C_{14}$aryl which is substituted by $C_1$–$C_{12}$alkyl, $C_1$–$C_{12}$alkoxy, $C_1$–$C_{12}$alkylthio, $C_1$–$C_{12}$alkylsulfinyl, $C_1$–$C_{12}$alkylsulfonyl, phenyl, benzyl, phenylsulfinyl, benzylsulfinyl, phenylsulfonyl, benzylsulfonyl, —CN, —$CF_3$, halogen, —$SO_3R_7$, —CO—$R_7$, —$CO_2R_7$, —CON($R_8$)$_2$, —N($R_8$)$_2$, or one of the RO— groups is H;

$R_1$, $R_2$, $R_3$ and $R_4$ are each independently of the other H, $C_1$–$C_{18}$alkyl, $C_1$–$C_{18}$alkoxy, $C_1$–$C_{18}$alkylthio, $C_1$–$C_{18}$alkylsulfinyl, $C_1$–$C_{18}$alkylsulfonyl, phenyl, benzyl, phenylthio; benzylthio, phenylsulfinyl, benzylsulfinyl, phenylsulfonyl, benzylsulfonyl, —CN, —$CF_3$, halogen,—$SO_3R_7$,—CO—$R_7$, —$CO_2R_7$, —CON($R_8$)$_2$ or —N($R_8$)$_2$;

$R_7$ is H, $C_1$–$C_{18}$alkyl, cyclohexyl, cyclopentyl, phenyl, $C_1$–$C_{12}$alkylphenyl, benzyl or $C_1$–$C_{12}$alkylbenzyl; and the $R_8$ substituents are each independently of the other H, $C_1$–$C_{18}$alkyl, cyclohexyl, cyclopentyl, phenyl, $C_1$–$C_{12}$alkylphenyl, benzyl, $C_1$–$C_{12}$alkylbenzyl, or one $R_8$ is H and the other $R_8$ is the —CO—$R_9$ group, wherein $R_9$ independently has the meaning of $R_7$, or both $R_8$ substituents, taken together, are tetramethylene, pentamethylene, 3-oxa-1,5-pentylene or the radical of formula —$CH_2CH_2$—N($C_1$–$C_6$alkyl)$CH_2CH_2$—, wherein one of the substituents $R_1$, $R_2$, $R_3$ and $R_4$ is a group of formula III

or R is substituted by a group of formula III, wherein X is a linking group or —X—C(O)— is a direct bond, and $R_5$ and $R_6$ are each independently of the other H, halogen, $C_1$–$C_{12}$alkyl or $C_6$–$C_{10}$aryl.

R is preferably unsubstituted or substituted $C_6$–$C_{10}$aryl, phenyl, 1- or 2-naphthyl. The preferred meaning of R is unsubstituted or substituted phenyl.

The group R can carry one or more than one substituent, preferably 1 to 3 substituents. If R is substituted by alkyl, alkoxy, alkylthio, alkylsulfinyl or alkylsulfonyl, alkyl may be linear or branched and may preferably contain 1 to 6, more particularly 1 to 4, carbon atoms. Illustrative examples are methyl, ethyl, the isomers of propyl, butyl, pentyl, hexyl, heptyl, octyl, nonyl, decyl, undecyl, dodecyl and the corresponding alkoxy, alkylthio, alkylsulfinyl and alkylsulfonyl radicals. Methyl, ethyl, n- and isopropyl, n-, iso- and tert-butyl, methoxy, ethoxy, methylthio, ethylthio, methyl- and ethylsulfinyl, as well as methyl- and ethylsulfonyl, are preferred.

Halogen as substituent of R is preferably —Br, —Cl and —F.

If R is substituted, the substituents are preferably selected from the group consisting of $C_1$–$C_4$alkyl, $C_1$–$C_4$alkoxy, phenyl, benzyl, —$CF_3$, F, Cl, Br, —$SO_3R_7$ and —$CO_2R_7$, where $R_7$ is preferably $C_1$–$C_4$alkyl.

In a particularly preferred embodiment of the invention, R is unsubstituted phenyl or phenyl which is substituted by the group of formula III.

$R_1$, $R_2$, $R_3$ and $R_4$ defined as alkyl, alkoxy, alkylthio, alkylsulfinyl, alkylsulfonyl contain preferably 1 to 12, most particularly 1 to 8 and, most preferably, 1 to 4, carbon atoms in the alkyl moiety. Typical examples of preferred substituents are methyl, ethyl, n- and isopropyl, n-, iso- and tert-butyl, methoxy, ethoxy, methylthio, ethylthio, methyl- and ethylsulfinyl, as well as methyl- and ethylsulfonyl.

$R_1$, $R_2$, $R_3$ and $R_4$ defined as halogen are preferably F, Cl or Br and, most preferably, Cl.

$R_7$ as alkyl is preferably $C_1$–$C_{12}$alkyl and, most preferably, $C_1$–$C_6$alkyl. Alkyl may be linear or branched. Preferred examples are methyl, ethyl, n- and isopropyl, n-, iso- and tert-butyl, n-pentyl and n-hexyl. $R_7$ as alkylphenyl is preferably $C_1$–$C_4$alkylphenyl and, as alkylbenzyl, is preferably $C_1$–$C_4$alkylbenzyl. Preferred examples are methylphenyl, ethylphenyl, dimethylphenyl, n- or isopropylphenyl, n- iso- or tert-butylphenyl, methylbenzyl, ethylbenzyl, dimethylbenzyl, n- or isopropylbenzyl, n-, iso- or tert-butylbenzyl.

$R_8$ as alkyl is preferably $C_1$–$C_{12}$alkyl and, most preferably, $C_1$–$C_6$alkyl. Alkyl may be linear or branched. Preferred examples are methyl, ethyl, n- and isopropyl, n-, iso- and tert-butyl, n-pentyl and n-hexyl. $R_8$ as alkylphenyl is preferably $C_1$–$C_4$alkylphenyl and, as alkylbenzyl, is preferably $C_1$–$C_4$alkylbenzyl. Preferred examples are methylphenyl, ethylphenyl, dimethylphenyl, n- or isopropylphenyl, n- iso- or tert-butylphenyl, methylbenzyl, ethylbenzyl, dimethylbenzyl, n- or isopropylbenzyl, n-, iso- or tert-butylbenzyl.

In a preferred embodiment of the invention, $R_1$, $R_2$, $R_3$ and $R_4$ are each independently of one another H, $C_1$–$C_4$alkyl, $C_1$–$C_4$alkoxy, $C_1$–$C_4$alkylthio, phenyl, benzyl, phenylthio, benzylthio, —$CF_3$, F, Cl, Br, —$SO_3R_7$, —$CO_2R_7$ or —$CO(NR_8)_2$, where $R_7$ is preferably $C_1$–$C_4$alkyl and the $R_8$ substituents are preferably each independently of each other H or $C_1$–$C_4$alkyl.

X as linking group may have the formulae —$R_9$—O—, —$R_9NR_{10}$—, —O—$R_9$—O—, —CO—O—$R_9$—O—, —CO—O—$R_9$—$NR_{10}$—, —CO—$NR_{10}$—$R_9$—O— or —CO—$NR_{10}$—$R_9$—$NR_{10}$—, wherein $R_9$ is linear or branched $C_2$–$C_{12}$alkylene, and $R_{10}$ is H, $C_1$–$C_6$alkyl, phenyl or benzyl.

$R_9$ is preferably $C_2$–$C_8$alkylene and, most preferably, $C_2$–$C_6$alkylene. Illustrative examples are ethylene, 1,2- or 1,3-propylene, 1,2-, 1,3- or 1,4-butylene, 1,5-pentylene and 1,6-hexylene. Alkylene is preferably linear. Particularly preferred examples are ethylene, 1,3-propylene and 1,4-butylene.

$R_{10}$ as alkyl is preferably $C_1$–$C_4$alkyl, typically methyl or ethyl. $R_{10}$ is most preferably H.

$R_5$ and $R_6$ as halogen are preferably Cl.

$R_5$ and $R_6$ as alkyl are preferably $C_1$–$C_6$alkyl and, most preferably, $C_1$–$C_4$alkyl. Illustrative examples are methyl, ethyl, propyl and butyl. Most preferably alkyl is methyl.

$R_5$ and $R_6$ as aryl are preferably phenyl.

In a preferred embodiment of the invention, $R_5$ and $R_6$ are H, methyl, ethyl, Cl or phenyl. In a particularly preferred embodiment of the invention, $R_5$ is H or methyl and $R_6$ is H. A preferred subgroup of compounds of formulae I and II is comprised of those wherein R is unsubstituted phenyl, and $R_1$, $R_2$, $R_3$ and $R_4$ are each independently of one another H, Cl, $C_1$–$C_4$alkyl, $C_1$–$C_4$alkoxy, $C_1$–$C_4$alkylthio, phenoxy or phenylthio, with the proviso that one of $R_1$, $R_2$, $R_3$ and $R_4$ is a group of formula III, or the substituent R is substituted by a group of formula III, wherein X is the radical of formula —$R_9$—O—, —O—$R_9$—O— or —CO—O—$R_9$—O—, $R_9$ is $C_2$–$C_6$alkylene, $R_5$ is H or methyl, and $R_6$ is H, methyl, ethyl or phenyl. Most preferably $R_5$ is H or methyl and $R_6$ is preferably H.

In another of its aspects, the invention relates to a process for the preparation of the compounds of formulae I and II, which comprises a) reacting a compound of formula IV or IVa

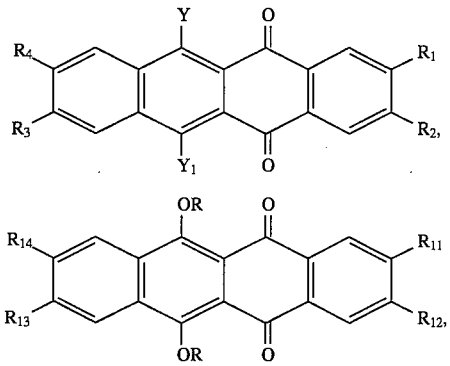

wherein R, $R_1$, $R_2$, $R_3$ and $R_4$ as well as the group RO— in formula IVa are as previously defined, Y and one of $R_{11}$ to $R_{14}$ is Cl, Br or $NO_2$ and the other substituents $R_{11}$ to $R_{14}$ have the meaning of $R_1$ to $R_4$, and $Y_1$ is H or has the meaning of Y, with equivalent amounts of a compound of formula V

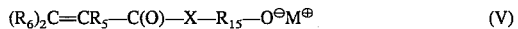

in the presence of a polar aprotic or protic solvent and at elevated temperature, wherein $R_5$ and $R_6$ have the given meanings, $R_{15}$ is $C_6$–$C_{14}$arylene which is unsubstituted or substituted by $C_1$–$C_{12}$alkyl, $C_1$–$C_{12}$alkoxy, $C_1$–$C_{12}$alkylthio, $C_1$–$C_{12}$alkylsulfinyl $C_1$–$C_2$alkylsulfonyl, phenyl, benzyl, phenylsulfinyl, benzylsulfinyl, phenylsulfonyl, benzylsulfonyl,—CN,-$CF_3$, halogen,—$SO_3R_7$,—CO—$R_7$,—$CO_2R_7$,  —$CON(R_8)_2$, —$N(R_8)_2$ —X—and —X—C(O)— are as previously defined, and $M^⊕$ is an alkali metal cation or an ammonium cation, or b) reacting a compound of formula VI or VIa

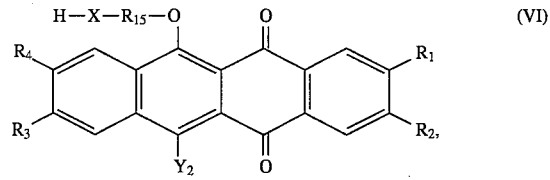

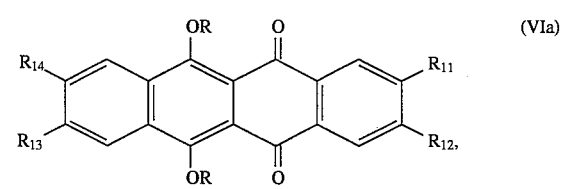

wherein $R_1$ $R_4$, R, $X_1$, a group RO—, $Y_2$ is H or the group —O—$R_{15}$—X—H, $R_{11}$ to $R_{14}$ are as previously defined, and one of $R_{11}$ to $R_{14}$ is the group —X—H, with equimolar amounts of the compound of formula VII

wherein $R_5$ and $R_6$ are as previously defined, and Z is Cl, Br o $C_1$–$C_4$alkoxy, and c) to prepare the compounds of formula II, irradiating the compounds of formula I with light of wavelength 300 to 450 nm.

$M^⊕$ is $Li^⊕$, $Na^⊕$, $K^⊕$ and tertiary ammonium, typically triethylammonium, trimethylammonium, tri-n-propylammonium or tri-n-butylammonium.

The inventive process a) is preferably carded out in the temperature range from 50° to 200° C., most preferably from 50° to 150° C. The salts of formula (V) can be used as such or produced in situ in the reaction mixture by reacting a suitable phenol with an alkali metal base or an alkali metal carbonate. The salts can be used in equimolar amounts or in excess, conveniently in an excess of up to 40% molar.

Illustrative examples of suitable solvents are N-substituted carboxamides and lactams (e.g. dimethyl formamide or N-methylpyrrolidone), sulfoxides and sulfones (e.g. dimethyl sulfoxide, tetramethylenesulfone) or ethers (including n-dipropyl ether, n-dibutyl ether, tetrahydrofuran or dioxane). The reaction may also be carried out in an excess of a phenol of formula V, which then simultaneously acts as solvent.

The compounds of formulae I and II are isolated and purified by conventional methods such as crystallisation and recrystallisation, or by chromatographic methods.

The esterification and amidation process of step b) are commonly known standard procedures. The reactions are ordinarily carded out in the presence of inert solvents such as halogenated hydrocarbons or ethers. When using carbonyl halides of formula VII it is expedient to use bases such as triethylamine to bind the hydrogen halides that form. In transesterification processes, the alkanols that form can be removed during the reaction by distillation, in some cases by azeotropic distillation.

The naphthacenediones of formulae IV and VIa, the vinyl phenols of formula V, in which —X—C(O)— is a direct bond, and the carboxylic acid derivatives of formula VII are known or can be prepared by known methods.

Some of the compounds of formulae VI and VIa are known or can be prepared by per se known methods, typically by esterifying or amidating appropriate carboxylic acid derivatives or their esters or amide-forming derivatives with diols or mono-protected diols, aminoalcohols or diamines. The compounds containing the —O—$R_9$—OH group can be obtained by etherification of corresponding hydroxyl group containing naphthacenediones with epoxides. The phenolates of formula V, where X is a linking group, can be prepared in the same manner from arylenediols or hydroxyarylenecarboxylic acids or acid derivatives.

The compounds of formula I are normally crystalline, thermally stable solids which are colourless to pale yellow in colour. They are soluble in organic solvents and in polymers. They are effective colour indicators for photopolymerisable systems which contain ethylenically unsaturated double bonds. Further, the compounds of formula I are reversibly photochromic.

When the compounds of formula I are irradiated, alone or incorporated in a substrate, with light having a wavelength of ca. 300 to 450 nm, a pronounced change in colour towards orange to red is observed. The change in colour derives from the photochemical conversion of the paraquinones of this invention into the corresponding anaquinones of formula II. The rate of conversion is surprisingly high and, depending on the amount, thickness of the sample and irradiation intensity, can be less than 3 seconds. The anaquinones of formula II are thus obtainable by irradiation of the paraquinones of formula I. The photochemical conversion is reversible. If the anaquinones are irradiated with light in the range of the wavelength of the new absorption band of longer wavelength at above 450 nm, then a back reaction to the colourless to yellow paraquinones is observed.

Surprisingly, the compounds of formulae I and II are radically polymerisable without loss of their reversible photochromic properties. They can therefore be used per se for the preparation of homopolymers or as comonomers for the preparation of copolymers.

In yet another of its aspects, the invention relates to homo- and copolymers containing, based on the polymer, a) 0.01 to 100% molar of at least one structural unit of formula VIII

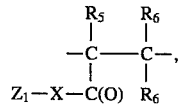

wherein $R_5$, $R_6$ and X are as previously defined, and $Z_1$ is a radical of formula Ia, Ib, IIa or

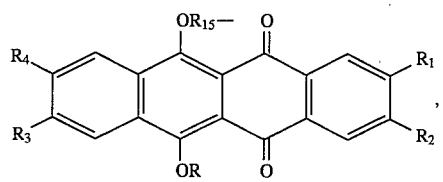

wherein $R_1$, $R_2$, $R_3$, $R_4$, $R_{15}$, R and the RO- group have the given meanings, one of $R_{16}$ to $R_{19}$ is a bond and the others have the meanings of $R_1$ to $R_4$, and b) 99.99 to 0% molar of at least one structural unit of formula IX

—A— (IX), wherein A is a radical of an olefin monomer that differs from formula VIII.

The inventive polymer preferably contains 0.1 to 100% molar, more preferably 1 to 100% molar, more preferably still 2 to 100% molar, even more preferably 5 to 90% molar and, most preferably, 1 to 50% molar, of structural units of formula VIII and preferably 99.9 to 0% molar, more preferably 99 to 0% molar, more preferably still 98 to 0% molar, even more preferably 95 to 10% molar and, most preferably, 99 to 50% molar, of structural units of formula IX. Among the copolymers, those are especially preferred that contain 1 to 30% molar and, most preferably, 1 to 20% molar, of structural units of formula VIII and 99 to 70% molar, most preferably 99 to 80% molar, of structural units of formula IX.

Th polymers may have an average molecular weight of 1000 to 2 000 000, preferably of 5000 to 1 000 000 and, most preferably, of 10 000 to 500 000.

The polymers are colourless to yellowish and in general amorphous and transparent. They are thermoplastics which can be processed by the standard shaping methods.

The preferred meanings given above apply to the structural units of formula VIII.

Innumerable olefin monomers from which the structural units —A— of formula IX are derived are known. Preferably —A— is ethylene which is unsubstituted or substituted by halogen, OH, CN, $C_1$–$C_4$alkyl, phenyl, $C_1$–$C_4$alkylphenyl, $C_1$–$C_4$alkoxyphenyl, halophenyl, hydroxyphenyl, $C_1$–$C_4$alkylhydroxyphenyl, $C_1$–$C_4$alkoxyhydroxyphenyl, chloro- or bromohydroxyphenyl, $C_1$–$C_4$alkoxy, phenoxy, $C_1$–$C_4$alkylphenoxy, benzyl, benzyloxy, —COO$^\ominus$M$^\oplus$, —COO$R_{20}$, —COB$R_{21}$—OH or —OCO—$R_{20}$, wherein M$^\oplus$ is H$^\oplus$, an alkali metal cation or an ammonium cation, $R_{20}$ is $C_1$–$C_{18}$alkyl, $C_5$–$C_7$cycloalkyl, ($C_1$–$C_{12}$alkyl)-$C_5$–$C_7$-cycloalkyl, phenyl, ($C_1$–$C_{12}$alkyl)phenyl, benzyl or ($C_1$–$C_{12}$alkyl)benzyl, $R_{21}$ is linear or branched $C_2$–$C_{18}$alkylene, poly($C_2$–$C_6$oxaalkylene) of 2 to 6 oxaalkylene units, $C_5$–$C_8$cycloalkylene, phenylene, benzylene or xylylene, and B is —O— or —NH—.

$R_{20}$ may be linear or branched $C_1$–$C_{18}$alkyl, $C_1$–$C_{12}$alkyl and, preferably, $C_1$–$C_6$alkyl. $R_{20}$ as cycloalkyl is preferably cyclopentyl or cyclohexyl. $R_{20}$ as ($C_1$–$C_{12}$alkyl)cycloalkyl is cycloalkyl, preferably cyclopentyl or cyclohexyl, and the alkyl moiety may be linear or branched and contains preferably 1 to 6, more particularly 1 to 4, carbon atoms. Where $R_{20}$ is alkylphenyl or alkylbenzyl, the alkyl moiety may be linear or branched and preferably contains 1 to 6, preferably 1 to 4, carbon atoms.

$R_{21}$ as alkylene contains preferably 2 to 12, more particularly 2 to 8 and, most preferably, 2 to 6 carbon atoms. Typical examples are ethylene and the isomers of propylene, butylene, pentylene, hexylene, heptylene, octylene, nonylene, decylene, undecylene, dodecylene, tetradecylene, hexadecylene and octadecylene. Preferred alkylene groups are ethylene, 1,2- and 1,3-propylene, 1,2-, 1,3- and 1,4-butylene, 1,2-, 1,3-, 1,4- and 1,5-pentylene and 1,2-, 1,3-, 1,4-, 1,5- and 1,6-hexylene.

$R_{21}$ as poly(oxaalkylene) preferably contains 2 to 4 oxaalkylene units and preferably 2 to 4, most preferably 2 or 3, carbon atoms in the alkylene moiety.

$R_{21}$ as cycloalkylene is preferably cyclopentylene or cyclohexylene.

In a preferred embodiment, A represents structural units of formula X

wherein $R_{24}$ is H, $C_{1-C6}$alkyl, —COOR$_{20}$ or —COO$^\ominus$M$^\oplus$, $R_{22}$ is H, F, Cl, CN or $C_{1-C6}$alkyl, $R_{23}$ is H, F, Cl, CN, $R_5$—O—, $C_{1-C12}$alkyl, —OH, —COO$^\ominus$M$^\oplus$, —COOR$_{20}$, —COBR$_{21}$—OH, —OCO—R$_{20}$, phenyl or phenyl which is substituted by —OH and/or one or two methyl or methoxy groups or one or two chlorine or bromine atoms, M$^\oplus$ is H$^\oplus$, an alkali metal cation or an ammonium cation, $R_{20}$ is $C_1$–$C_{18}$alkyl, $C_5$–$C_7$cycloalkyl, ($C_1$–$C_{12}$alkyl)-$C_5$–$C_7$cycloalkyl, phenyl, ($C_{1-C12}$alkyl)phenyl, benzyl or ($C_1$–$C_{12}$alkyl)benzyl, $R_{21}$ is linear or branched $C_2$–$C_{18}$alkylene, poly($C_2$–$C_6$oxaalkylene) containing 2 to 6 oxaalkylene units, $C_5$–$C_8$cycloalkylene, phenylene, benzylene or xylylene, and B is —O— or —NH—.

$R_{24}$ is preferably H. $R_{24}$ as alkyl is preferably methyl or ethyl. If $R_{24}$ is —COOR$_{20}$, $R_{20}$ is preferably $C_1$–$C_{12}$ alkyl, more particularly $C_1$–$C_6$alkyl.

$R_{22}$ as alkyl is preferably $C_1$–$C_4$alkyl, typically methyl, ethyl, n-propyl and n-butyl. The preferred meaning of $R_{22}$ is H, Cl or $C_{1-C4}$-Alkyl.

If $R_{23}$ is the group $R_{20}$—O—, $R_{20}$ is preferably $C_1$–$C_{12}$alkyl, most preferably $C_1$–$C_6$alkyl. $R_{23}$ as alkyl contains preferably 1 to 6, more particularly 1 to 4, carbon atoms. If $R_{23}$ is the group —COOR$_{20}$, $R_{20}$ is preferably $C_1$–$C_{12}$alkyl, more particularly $C_{1-C6}$alkyl, cyclopentyl or cyclohexyl. If $R_{23}$ is the group —OCO—R$_{20}$, $R_{20}$ is preferably $C_{1-C12}$alkyl, more particularly $C_1$–$C_6$alkyl, phenyl or benzyl.

If $R_{23}$ is the group —COOR$_{21}$OH, then the preferred meanings previously assigned to $R_{21}$ apply.

In a preferred embodiment, $R_{24}$ is H, $R_{22}$ is H, F, Cl, methyl or ethyl, and $R_{23}$ is —F, —Cl, —CN,—OH, $C_1$–$C_4$alkyl, $C_1$–$C_6$alkoxy,—COO—$C_{1-C6}$alkyl, —COO—$R_{21}$—OH,—COOM$^\oplus$ —OOC—$C_1$–$C_6$alkyl, phenyl, methylphenyl, dimethylphenyl, chlorophenyl, dichlorophenyl, dibromophenyl, methoxyphenyl, dimethoxyphenyl, hydroxyphenyl, or phenyl or phenyl which is substituted by —OH and/or one or two methyl or methoxy groups or one or two chlorine or bromine atoms, and M$^\oplus$ is trialkylammonium containing 1 to 4 carbon atoms in the alkyl moieties, and $R_{21}$ is $C_2$–$C_6$alkylene.

The novel copolymers are block polymers or copolymers with random distribution of the structural units.

The novel polymers can be obtained in known manner by radical polymerisation of the monomers and, in some cases, the comonomers. Depending on the consistency of the reaction mixtures, the reactions can be carried out without or with addition of an inert solvent. The polymerisation is ordinarily initiated by radical-forming initiators and then terminated at elevated temperature. The polymerisation can also be carried out by irradiation with light, especially UV radiation. This is especially expedient if it is desired to polymerise layers of the polymerisable monomers or mixtures of monomers present on a substrate. The photopolymerisation is normally carried out in the presence of photoinitiators or sensitisers. The monomers of this invention may themselves have this action.

Surprisingly, the novel polymers have the same photochromic properties as the monomers. They are soluble in organic solvents. They are also thermally stable, have low susceptibility to oxidation and are miscible with polymers. In contradistinction to monomeric, photochromic compounds, no dehomogenisation is observed even at higher concentrations. Like their monomers, the novel polymers are also effective colour indicators for photopolymerisable systems which contain ethylenically unsaturated double bonds.

When the novel polymers are irradiated, alone or incorporated in a substrate, with light having a wavelength of ca. 300 to 450 nm, a pronounced change in colour towards orange to red is observed. The change in colour derives from the photochemical conversion of the paraquinone structure to the corresponding anaquinone structure. The rate of conversion is surprisingly high and, depending on the amount, thickness of the sample and irradiation intensity, can be less than 3 seconds. The novel anaquinones are thus obtainable by irradiation of the paraquinones. The photochemical conversion remains reversible. If the anaquinones are irradiated with light in the range of the wavelength of the new absorption band of longer wavelength (<450 nm), then a back reaction to the colourless to yellow paraquinones is observed. It is especially advantageous that this procedure can be repeated several times. The stability of the photochemical conversion of paraquinones to anaquinones and the back reaction to paraquinones is surprisingly high and the fatigue even in air or in substrates is correspondingly low. Thus virtually no changes are observed in more than 20 cycles. It is also advantageous that the light absorption necessary for the photochemical conversion lies in the range of the wavelength of commercially available lasers.

The invention further relates to the use of compounds of formula I or II or the polymers containing the structural units of formulae VIII and IX as reversible photochromic structures for contrast formation or light absorption.

The compounds of formula I or I1 or the polymers containing the structural units of formulae VIII and IX can be used as colour indicators in photopolymerisible systems. Thus it is possible to mark irradiated products (for example protective layers, printing plates, offset printing plates, printed circuits, solder masks) and to distinguish them from non-irradiated products and, in product control, to sort out imperfectly irradiated products before or after development.

The compounds of formula I II or the polymers containing the structural units of formulae VIII and IX can also be used by themselves, in solution or incorporated in polymers as photochemically modifiable colour indicators or as photochemically modifiable circuit components.

The compounds of formula I II or the polymers containing the structural units of formulae VIII and IX can also be used in organic or inorganic glasses as photochemically modifiable colour filters, for example in glasses for sunglasses, contact lenses, windows and mirrors.

The invention further relates to a radiation-sensitive composition comprising a) a radiation-sensitive organic material, and b) at least one compound of formula I or II or at least one polymer containing the structural units of formulae VIII and IX.

The novel composition may contain the compounds of formulae I and II or the polymers containing the structural units of formulae VIII and IX in an amount of 0.001 to 20% by weight, preferably 0.001 to 10% by weight and, most preferably, 0.01 to 5% by weight, based on component a).

Radiation-sensitive and hence also photostructurable materials are known. They may be positive or negative systems. Such materials are described, for example, by E. Green et al. in J. Macromol. Sci.; Revs. Macromol. and Chem., C21(2), 187–273 (1981 to 1982) and by G. A. Delzenne in Adv. Photochem., 11, S. 1–103 (1979).

The radiation-sensitive organic material is preferably a1) a non-volatile monomeric, oligomeric or polymeric substrate containing photopolymerisable or photodimerisable ethylenically unsaturated groups, a2) a cationically curable system, or a3) photocrosslinkable polyimides.

Radically polymerisable monomers in conjunction with the compounds of formula I or II are especially preferred, as these are concurrently incorporated by polymerisation.

Such photopolymerisable substances are typically acrylates and, preferably, methacrylates of polyols, for example ethylene glycol, propanediol, butanediol, hexanediol, bis(hydroxymethyl)cyclohexane, polyoxyalkylenediols such as di-, tri- or tetraethylene glycol, di- or tri-1,2-propylene glycol, trimethylolmethane, trimethylolethane or trimethylolpropane and pentaerythritol, which may be used by themselves, in mixtures and in admixture with binders.

Exemplary photodimerisable substances are homo- and copolymers which contain cinnamic acid groups or substituted maleimidyl compounds in side groups or chalcone groups in the polymer chain.

Such compositions are typically those wherein component a1) is a homo- or copolymer of acrylates, methacrylates or maleates the ester groups of which contain a radical of formula

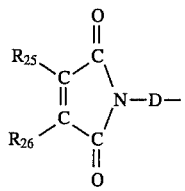

wherein C is linear or branched unsubstituted or hydroxyl-substituted $C_2$–$C_{12}$alkylene, cyclohexylene or phenylene, and $R_{25}$ and $R_{26}$ are each independently of the other chloro or bromo, phenyl or $C_1$–$C_4$alkyl, or $R_{25}$ and $R_{26}$, when taken together, are trimethylene, tetramethylene or

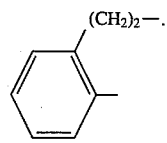

Such polymers are disclosed, inter alia, in U.S. Pat. No. 4,193,927.

The photopolymerisable or photodimerisable substances may contain further additives customarily used for processing or application, as well as other photoinitiators or photosensitisers.

The cationically curable systems are preferably epoxy compounds containing at least two epoxy groups in the molecule and in which a photoinitiator is incorporated. Suitable photoinitiators are typically cyclopentadienylarene metal salts, cyclopentadienyl metal carbonyl salts and onium salts which are described in the above mentioned publications. The curable systems may contain additives customarily used for processing and application.

Photosensitive polyimides are disclosed, for example, in DE-A-1 962 588, EP-A-0 132 221, EP-A-0 134 752, EP-A-0 162 017 and EP-A-0 182 745.

The composition of this invention is applied by known methods as layer to substrates and either a protective layer is produced by irradiation over the surface, or a relief image is produced by irradiation through a photomask or by locally defined irradiation with a guided laser beam or by holographic methods and subsequent development.

In another of its aspects, the invention relates to a composition comprising a) a colourless organic solvent, a polymer or an organic glass or a compound glass, and b) dissolved, incorporated therein or present as layer on at least one surface, a compound of formula I or II or at least one polymer containing the structural units of formula VIII or IX. Component b) is preferably present in an mount of 0.001 to 20% by weight, preferably 0.001 to 10% by weight and most preferably, 0.01 to 5% by weight, based on component a). Organic solutions can be used for coating other substances, for example solid substrates such as inorganic glasses which can then be used as photochemically modifiable substrates. The compounds of formula I or II can also be sublimed on to substrates. The coated substrates may be provided with a protective layer of transparent polymers. Solid substrates can also be coated with compositions which contain a polymer and at least one compound of formula I or II or at least one polymer containing the structural units of formula VIII or IX. Suitable solvents are typically hydrocarbons, halogenated hydrocarbons, ketones, carboxylic acid esters and lactones, N-alkylated acid amides and lactams, alkanols and ethers.

Illustrative examples of suitable polymers are thermoset plastics, thermoplastics and structurally crosslinked polymers. The polymers are preferably transparent. Those skilled in the art are familiar with such polymers and organic glasses. The incorporation of the compounds of the invention is effected by known methods, conveniently by dissolving methods and removing the solvent, calendering or extrusion. The compounds of this invention can also be incorporated in the substrates before, during or after their synthesis.

The invention also relates to a process for the preparation of coloured materials by exposure to light, which comprises incorporating a compound of formula I or II or a polymer containing the structural units of formula VIII or IX in the material and then irradiating said material with light.

The invention further relates to the use of compounds of formula I or II or of the polymers containing the structural units of formula VIII or IX as colour indicators or photochemically modifiable colour filters upon exposure to light.

In another of its aspects, the invention relates to the use of a compound of formula I or II or of the polymers containing the structural units of formula VIII or IX for the reversible optical storage of information, which information is written with light, preferably laser light, into a memory-active layer containing said compound. The written information can be erased, preferably with laser light, thus affording the possibility of cyclic writing-in and erasing. To produce a memory-active layer, the compound of formula I or II or the polymer containing the structural units of formula VII or IX can be dissolved in a transparent matrix by methods desribed above and applied in a thin layer to a flat substrate. The thickness of the memory-active layer is ca. 0.1–100 µm, preferably 0.3–3 µm.

Suitable substrates are typically metals, alloys, glass, minerals, ceramics and thermoset or thermoplastic materials. The substrate may have a thickness of 0.01 mm to 1 cm, preferably of 0.1 mm to 0.3 cm. Preferred substrates are glass and homopolyeric or copolymeric plastics materials. Suitable plastics materials include thermoplastic polycarbonates, polyamides, polyesters, polyacrylates and polymethacrylates, polyurethanes, polyolefins, polyvinyl chloride, polyvinylidene fluoride, polyimides, thermoset polyesters and epoxy resins.

The substrate may be provided with one or more than one layer of dithioquinacridone, typically with 1 to 10, preferably 1 to 5 and, most preferably, 1 to 3, layers. The number of layers and further layers will depend mainly on the optical density of the layer arrangement, which must ensure a sufficient transmission at the wavelength used for recording.

The memory-active layer or the substrate can be coated with a reflective layer which has a thickness of typically 100 to 5000 Å, preferably 100 to 3000 Å and, most preferably, 300 to 1500 Å. Particularly suitable reflective materials are metals which reflect the laser light used for recording and reproduction well. A reflective layer of aluminium or gold is especially preferred on account of the high reflectivity and the ease with which it can be prepared.

The topmost layer, depending on the layer structure, conveniently the reflective layer, the memory-active layer or a further auxiliary layer, is preferably coated with a protective layer that may have a thickness of 0.1 to 100 Åµm, preferably 0.1 to 50 Åµm and, most preferably, 0.5 to 15 Åµm. Mainly suitable for use as protective material are plastics materials that are coated in a thin layer either direct or with the aid of adhesive layers on to the substrate or the topmost layer. It is best to choose mechanically and thermally stable plastics materials which have good surface properties and may be additionally modified, for example marked. The plastics materials may be thermoset and thermoplastic materials. Radiation-cured (e.g. UV cured) protective layers which are particularly easy and economical to prepare are preferred. Innumerable radiation-curable materials are known. Illustrative examples of radiation-curable monomers and oligomers are acrylates and methacrylates of diols, triols and tetrols, polyimides from aromatic tetracarboxylic acids and aromatic diamines containing $C_1$–$C_4$alkyl groups in at least two ortho-positions of the amino groups, and oligomers containing dialkyl groups, conveniently dimethylmaleimidyl groups. Specific examples are UV-crosslinkable polymers derived from polyacrylates, such as RENGOLUX® RZ 3200/003 or 3203/001, available from Morton International-Dr. Renger.

Suitable coating techniques include immersion, casting, brushing, doctor coating, centrifugal casting, and vapour deposition methods which are carded out under vacuum. If, for example, casting methods are employed, solutions in organic solvents will normally be used, which solutions may additionally contain a binder. When using solvents, care must be taken that the substrates are inactive to these solvents. It is preferred to prepare all layers by vapour deposition, especially under vacuum. Suitable coating techniques are described, inter alia, in EP-A-0 401 791.

The structure of the recording material of this invention will depend mainly on the method of reading out: known techniques are measuring the change in transmission or reflection. If the recording system functions according to a change in light transmission, the structure may suitably comprise: transparent substrate/recording layer (one or more layers) and, if appropriate, transparent protective layer. The radiation for writing and reading out information can be applied either from the substrate side of the system or from the recording layer or protective layer side, the light detector always being on the adjacent side.

If the recording material is structured according to the change in reflectivity, then the following other layered structures are possible: transparent substrate/recording layer (one or more layers)/reflective layer and, if appropriate, protective layer (not necessarily transparent), or substrate (not necessarily transparent)/reflective layer/recording layer and, if appropriate, transparent protective layer. In the former case, the radiation is applied from the substrate side of the system, whereas in the latter case the radiation is applied from the recording layer or, if present, from the protective layer side of the system. In both cases, the light detector is on the same side as the light source. The first mentioned layer structure of the inventive recording material is generally preferred.

The information can be written by scanned, holographic or photographic irradiation of the memory-active layer with spectral, preferably coherent, laser light in the wavelength range of 300–550 nm.

Reading out can be effected with reduced irradiation intensity at the wavelength in which the information is written via the locally altered transmission, reflectance, refraction or fluorescence of the memory-active layer.

Erasure can be made by pin-point or spread irradiation of the memory-active layer in the wavelength range of 300–500 nm, depending on whether the memory-active layer contains paraquinones anaquinones.

One advantage of the utility of this invention is that the wavelengths necessary for writing in, reading out and erasing are in the range of commercially available lasers (for example argon ion lasers: 488/514 nm and 351/363 nm; neodym-YAG lasers: 532 nm and 355 nm; XeF excimer lasers: 351 nm; HeCd lasers: 325 and 442 nm, with frequency doubling and trebling).

A further advantage is the high contrast of absorption obtainable between the written and erased state in the range of 450–550 nm and the wide dynamic range associated therewith of the memory-active layer.

Another advantage is that the quantum yield when writing is fairly low, so that the danger of overwriting when reading out is greatly diminished.

Conversely, it is also advantageous that the quantum yield when erasing is fairly high, thus making possible a rapid erasure over a large area.

Yet a further advantage is that, when reading out, the quinones fluoresce and hence make possible a highly sensitive detection of the memory status via the fluorescence. The fact that the energy pulsed in for reading out dissipates substantially via the fluorescence and not thermally also counteracts an undesirable heating of the memory-active layer.

Another advantage is the high photochemical stability of the quinones and the great number of writing/erasing cycles thereby obtainable.

Finally, yet another advantage is the possibility of cyclic data refreshing by admixture of a suitable quantum of light of the erasure wavelength during reading out.

The invention is illustrated by the following Examples.

A Preparation of the Starting Compounds

EXAMPLE A1

Preparation of a mixture of (2-hydroxyethyl)-6,11 -diphenoxynaphthacene-5,12-dione-2- and-8-carboxylate isomers a) A Mixture of (2-hydroxyethyl)-6,11 -Dichloronaphthacene-5,12-dione-2- and -8-carboxylate isomers 4.8 g (12.5 mmol) of a mixture of 6,11-dichloronaphthacene-5,12-dione-2- and -8-carboxylic acid isomers are suspended in 50 ml of ethylene glycol and 2 ml of concentrated sulfuric acid are added to the suspension. The reaction mixture is stirred for 4 days at 120° C., cooled, and poured into water. The brown precipitate is isolated by filtration, washed with water and then purified by column chromatography [silica gel, methylene chloride/methanol (50:1)], giving 1.65 g (32%)of product.

b) Preparation of the Title Compound 21 mmol of the isomers a), 42 phenol of phenol and 52 mmol of anhydrous $K_2CO_3$ are suspended in 95 ml of dimethyl sulfoxide and the suspension is stirred for 5 h at 80° C. Afterwards the cooled reaction mixture is poured into water and extracted with diethyl ether. The organic phase is washed with water, then dried over $Na_2SO_4$ and concentrated. The residue is recrystallised from methylene chloride/hexane, giving the title compound in 33% yield. Melting point 143° C.

EXAMPLE A2

Preparation of 6,11-bis[4-(3-hydroxypropyl)phenoxy]naphthacene-5,12-dione.

a) 6,11-Bis[4-(3-tetrahydropyran-2-yloxypropyl)phenoxy]naphthacene-5,12dione.

21 mmol of 6, 11-dichloronaphthacene-5, 12-dione, 42 mmol of 4-(3-tetrahydropyran-2-yl-oxypropyl) phenol and 52 mmol of anhydrous $K_2CO_3$ are suspended in 95 ml of dimethyl sulfoxide and stirred for 5 h at 80° C. The cooled reaction mixture is afterwards poured into water and extracted with diethyl ether. The organic phase is washed with water, then dried over $Na_2SO_4$ and concentrated. The residue is recrystallised from methylene chloride/hexane, giving 72% of product; melting point 125°–130° C.

b) Preparation of the Title Compound 15.3 mmol of compound a) are suspended in a mixture of 170 ml of methanol and 100 ml of diethyl ether. After addition of 20 mg of toluenesulfonic acid monohydrate, the reaction mixture is stirred for 1 day at room temperature. Then methylene chloride is added and the organic solution is washed first with water and then with a saturated solution of sodium chloride and dried over $Na_2SO_4$. The organic solution is concentrated and the residue is dissolved once more in methylene chloride and a small mount of methanol. The product is precipitated by addition of hexane, isolated by filtration and vacuum dried, giving the title compound in 76% yield. Melting point 218°–220° C.

EXAMPLE A3

Preparation of 6,11-bis[4-(6-hydroxyhex-1-yloxycarbonyl)phenoxy]naphthacene-5, 12-dione.

The procedure of Example A2 is repeated, using 4-(6-tetrahydropyran-2-yloxyhex-1-yloxycarbonyl)phenol, giving 6, 11-bis[4-(6-tetrahydropyran-2-yloxyhex-1-yloxycarbonyl)phenoxy]naphthacene-5,12-dione in a yield of 71%, melting point 114°–117° C., and the title compound in a yield of 91%, melting point 172°–173° C.

EXAMPLE A4

Preparation of a mixture of 2- and 8-phenylthio-6, 11-bis[4-(3-hydroxypropyl) phenoxy]naphthacene-5, 12-dione isomers.

The procedure of Example A2 is repeated, using 4-(3-tetrahydropyran-2-yloxypropyl)-phenol and a mixture of 2- and 8-phenylthio-6,11-dichloronaphthacene-5,12-dione isomers, giving a mixture of 2- and 8-phenylthio-6,11-bis[4-(3-tetrahydropyran-2-yloxypropyl) phenoxy]naphthacene-5, 12-dione isomers in a yield of 54%, melting point 140°–148° C., and the title compounds in a yield of 69%, melting point 205°–213° C.

EXAMPLE A5

Preparation of a mixture of 2- and 8-phenylthio-6, 11-bis[4-(6-hydroxyhexyl-yloxycarbonyl) phenoxy] naphthacene-5,12-dione isomers.

The procedure of Example A2 is repeated, using 4-(6-tetrahydropyran-2-yloxyhex-1-yl-oxycaxbonyl)phenol and a mixture of 2- and 8-phenylthio-6, 11-dichloronaphthacene-5,12-dione isomers, giving a mixture of 2- and 8-phenylthio-6,11-bis[4-(6-tetrahydropyran-2-yloxyhex-1-yloxycarbonyl)phenoxy]naphthacene-5,12-dione isomers in a yield of 58%, melting point 90°–95° C., and the title compounds in a yield of 66%, melting point 140°–148° C.

B) PREPARATION OF THE NOVEL COMPOUNDS

EXAMPLE B1

Preparation of a mixture of 6,11-diphenoxynaphthacene-5,12-dione-2- and -8-methacroyloxyethylcarboxylate isomers 5.4 mmol of compound A1 are suspended in 50 ml of methylene chloride. To the suspension are added 21.6 mmol of triethylamine and the reaction mixture is cooled to 0° C. After addition of 22 mmol of methacrylyl chloride, the reaction mixture is stirred first for 20 min at 0° C. and for 2 h at room temperature. The reaction mixture is then heated with water, made alkaline with NaOH, and extracted with methylene chloride. The organic phase is washed with a solution of sodium chloride, then dried over $Na_2SO_4$ and concentrated. The residue is recrystallised from methylene chloride/hexane, giving the title compound in 92% yield in the form of yellow crystals with a melting point of 144°–146 C.

EXAMPLE B2

Preparation of 6,11-[4-(3-methacroyloxypropyl)phenoxy]naphthacene-5,12-dione.

The general procedure of Example B1 is repeated, using the compound A2, giving the title compound in 96% yield in the form of yellow crystals with a melting point of 166°–168° C.

EXAMPLE B3

Preparation of 6, 11-[4-(6-methacroyloxyhex-1-yloxycarbonyl)phenoxy]-naphthacene-5,12-dione.

The general procedure of Example B1 is repeated, using the compound A3, giving the title compound in 90% yield in the form of yellow crystals with a melting point of 117°–119° C.

EXAMPLE B4

Preparation of a mixture of 2- and 8-phenylthio-6, 11-[4-(3-methacroyloxy-propyl)phenoxy]naphthacene-5,12-dione isomers.

The general procedure of Example B1 is repeated, using the compound A4, giving the title compound in 59% yield in the form of yellow crystals with a melting point of 164°–166° C.

EXAMPLE B5

Preparation of a mixture of 2- and 8-phenylthio-6, 11-[4-(6-methacroyloxyhex-1-yloxycarbonyl)phenoxy]naphthacene-5,12-dione isomers.

The general procedure of Example B1 is repeated, using the compound A5, giving the title compound in 62% yield in the form of yellow crystals with a melting point of 105°–108° C.

C) USE OF THE NOVEL COMPOUNDS

EXAMPLE C1

50 g of 6,11-[4-(6-methacroyloxyhex-1-yloxycarbonyl)phenoxy]naphthacene-5,12-dione are dissolved in 1 g of dimethacrylate of ethoxybisphenol A warmed to 50° C. To the solution are then added 1 g of diglycidyl diacrylate of bisphenol A warmed to 50° C. and 10 mg of azoisobutyronitrile, and the batch is mixed, with stirring, until a clear yellow mixture is obtained.

The formulation is applied between two glass plates with 1 mm teflon spacer and cured for 20 h at 80° C.

The clear yellow plate is partially covered and irradiated with a 200 watt Hg short arc lamp for 2 min through a 420 mm long-pass filter. The irradiated zone exhibits a change in colour to orange. The exposed zone can be restored to the original colour by irradiation through a 515 nm long-pass filter.

What is claimed is:

1. A homopolymer or copolymer containing, based on the polymer, a) 0.01 to 100% molar of at least one structural unit of formula VIII

wherein $R_5$ and $R_6$ are each independently of the other H, halogen, $C_1$–$C_{12}$alkyl or $C_6$–$C_{10}$aryl, a linking group or —X—C(O)— is a direct bond, and $Z_1$ is a radical of formula Ia, Ib, IIa or IIb,

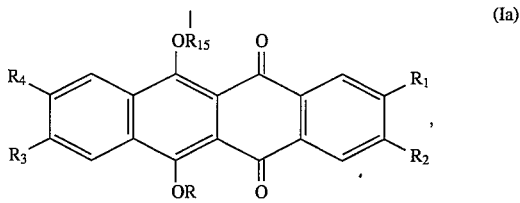

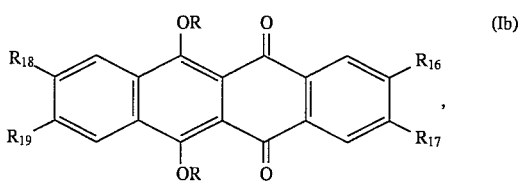

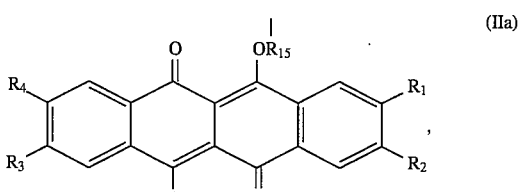

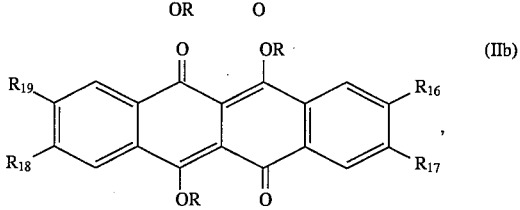

wherein $R_1$, $R_2$, $R_3$ and $R_4$ are each independently of the other H, $C_{1-C_{18}}$alkyl, $C_1$–$C_{18}$alkoxy, $C_1$–$C_{18}$alkylthio, $C_1$–$C_{18}$alkylsulfinyl, $C_1$–$C_{18}$alkylsulfonyl, phenyl, benzyl, phenylthio, benzylthio, phenylsulfinyl, benzylsulfinyl, phenylsulfonyl, benzylsulfonyl, —CN, —CF$_3$, halogen, —SO$_3$R$_7$, —CO—R$_7$, —CO$_2$R$_7$, —CON (R$_8$)$_2$, —N(R$_8$)$_2$ or a group of formula III

wherein one and only one of $R_1$, $R_2$, $R_3$ and $R_4$ is a group of formula III; $R_{15}$ is $C_1C_{14}$arylene which is unsubstituted or substituted by $C_1$–$C_{12}$alkyl, $C_1$–$C_{12}$alkoxy, $C_1$–$C_{12}$alkylthio, $C_1$–$C_{12}$alkylsulfinyl, $C_1$–$C_{12}$alkylsulfonyl, phenyl, benzyl, phenylsulfinyl, benzylsulfinyl, phenylsulfonyl, benzylsulfonyl, —CN, —CF$_3$, halogen, —SO$_3$R$_7$, —CO—R$_7$, —CO$_2$R$_7$, —CON(R$_8$)$_2$, or —N(R$_8$)$_2$; R is unsubstituted $C_6$–$C_{14}$aryl or $C_6$–$C_{14}$aryl which is substituted by $C_1$–$C_{12}$alkyl, $C_1$–$C_{12}$alkoxy, $C_1$–$C_{12}$alkylthio, $C_1$–$C_{12}$alkylsulfinyl, $C_1$–$C_{12}$alkylsulfonyl, phenyl, benzyl, phenylsulfinyl, benzylsulfinyl, phenylsulfonyl, benzylsulfonyl, —CN, —CF$_3$, halogen, —SO$_3$R$_7$, —CO—R$_7$, —CO$_2$R$_7$, —CON(R$_8$)$_2$, —N(R$_8$)$_2$,or one of the RO- groups is H, one of $R_{16}$ to $R_{19}$ is a bond to polymer backbone and the others have the meanings of $R_1$ to $R_4$, and b) 99.99 to 0% molar of at least one structural unit of formula IX $$-A-  \quad (IX),$$

wherein A is a radical of an olefin monomer that differs from formula VIII.

2. A polymer according to claim 1, which has a molecular weight of 1000 to 2 000 000 Dalton.

3. A polymer ccording to claim 1, wherein A is a structural unit of formula

(X)

wherein $R_{24}$ is H, $C_1-C_6$alkyl, $-COOR_{20}$ or $-COO^\ominus M^\oplus$, $R_{22}$ is H, F, Cl, CN or $C_1-C_6$alkyl, $R_{23}$ is H, F, Cl, CN, $R_5-O-$, $C_1-C_{12}$alkyl, $-OH$, $-COO^\ominus M^\oplus$, $-COOR_{20}$, $-COBR_{21}-OH$, $-OCO-R_{20}$, phenyl or phenyl which is substituted by $-OH$ and/or one or two methyl or methoxy groups or one or two chlorine or bromine atoms, $M^\oplus$ is $H^\oplus$, an alkali metal cation or an ammonium cation, $R_{20}$ is $C_1-C_{18}$alkyl, $C_5-C_7$cycloalkl, $(C_1-C_{12}$alkyl$)-C_5-C_7$cycloalkyl, phenyl,$(C_1-C_{12}$ alkyl$)$phenyl, benzyl or $(C_1-C_{12}$alkyl$)$benzyl, $R_{21}$ is linear or branched $C_2-C_{18}$alkylene, poly$(C_2-C_6$oxaalkylene$)$ containing 2 to 6 oxaalkylene units, $C_5-C_8$cycloalkylene, phenylene, benzylene or xylylene, and B is $-O-$ or $-NH-$.

4. A polymer according to claim 3, wherein $R_{24}$ is H.

5. A polymer according to claim 3, wherein $R_{22}$ is H, Cl or $C_1-C_4$alkyl.

6. A polymer according to claim 3, wherein $R_{23}$ is $R_{20}-O-$, $C_1-C_6$alkyl, $-COOR_{20}$, $-COOR_{21}OH$ or $-OCO-R_{20}$, and $R_{20}$ is $C_1-C_{12}$alkyl and $R_{21}$ is $C_2-C_{12}$alkylene.

7. A polymer according to claim 3, wherein $R_{24}$ is H, $R_{22}$ is H, F, Cl, methyl or ethyl, and $R_{23}$ is $-F, -Cl, -CN, -OH$, $C_1-C_4$alkyl, $C_{1-C6}$alkoxy, $-COO-C_{1-C6}$alkyl, $-COO-R_{21}-OH$, $-COOM^\oplus-OOC-C_1-C_6$alkyl, phenyl, methylphenyl, dimethylphenyl, chlorophenyl, dichlorophenyl, dibromophenyl, methoxyphenyl, dimethoxyphenyl, hydroxyphenyl, or phenyl or phenyl which is substituted by $-OH$ and/or one or two methyl or methoxy groups or one or two chlorine or bromine atoms, wherein $M^\oplus$ is trialkylammonium containing 1 to 4 carbon atoms in the alkyl moieties, and $R_{21}$ is $C_2-C_6$alkylene.

8. A method for the reversible optical storage of information, which comprises incorporating a homopolmer or copolymer of claim 1 in a memory active layer and irradiating the memory active layer with light.

9. A process for the preparation of a colored material, which comprises irradiating a homopolymer or copolymer of claim 1 with light.

10. A photochemically modifiable color filter which comprises a homopolymer or copolymer of claim 1.

* * * * *